US005106971A

United States Patent [19]
Kletecka et al.

[11] Patent Number: 5,106,971
[45] Date of Patent: Apr. 21, 1992

[54] HYBRID PROCESS FOR PREPARING A TRI-SUBSTITUTED TRIAZINE

[75] Inventors: George Kletecka, Fairview Park; Victor L. Ledesma; Ronald M. Kovach, both of Avon Lake, all of Ohio

[73] Assignee: The B. F. Goodrich Company, Akron, Ohio

[21] Appl. No.: 684,416

[22] Filed: Apr. 12, 1991

[51] Int. Cl.$^5$ .................. C07D 401/12; C07D 403/12
[52] U.S. Cl. .................. 544/198; 540/524; 540/575; 540/525; 544/209; 544/212; 544/219
[58] Field of Search ............. 544/198, 209, 212, 219; 540/524, 575, 525

[56] References Cited

U.S. PATENT DOCUMENTS

| | | | |
|---|---|---|---|
| 4,480,092 | 10/1984 | Lai et al. | 544/198 |
| 4,629,752 | 12/1986 | Layer et al. | 524/100 |
| 4,731,393 | 3/1988 | Karrer et al. | 522/117 |

*Primary Examiner*—John M. Ford
*Attorney, Agent, or Firm*—Mary Ann Tucker; Alfred D. Lobo

[57] ABSTRACT

The prior art solvent process for the manufacture of an oxo-piperazinyl triazine (PIP-T) compound required carrying out the reaction between an appropriately hindered cyclic amine and cyanuric chloride in the presence of caustic catalyst, in alkylbenzene solution, typically toluene. The chloride ions generated during the reaction, in presence of water present in the reaction zone, produced serious corrosion and resulted in off-color product which had a melt absorptivity greater than 3.5 mL/gm.cm. This "color" in the product made the product generally unmarketable. Another process to make a PIP-T termed "the solventless" process used no toluene solvent, and no caustic but required such a very large excess of amine that the catalytic function of the amine.HCl salt went unnoticed. In the novel process, referred to as the "hybrid" process, this catalytic function allows the use of only as much toluene in the reactor as is needed to keep the product formed and the excess amine in solution, and the use of less than a two-fold molar excess over the molar amount to displace each chlorine atom of the cyanuric chloride. The result is exceptionally high purity and yield with color no greater than that which the marketplace accepts.

24 Claims, 2 Drawing Sheets

HYBRID PROCESS FOR PREPARING A TRI-SUBSTITUTED TRIAZINE

BACKGROUND OF THE INVENTION

This invention relates generally to a process which requires recovery of a desirably white reaction product of a cyanuric halide with an amine reactant (white being indicative of the product's high purity), in high yield. The desired tri-substituted triazine compound must be white enough to meet industry standards because the compound is a prized stabilizer for a variety of synthetic resinous materials, and the market-place demands that the tri-substituted triazine not contribute any unwanted color to the stabilized material. The reason for requiring a high yield is that the amine used to make the tri-substitution is so costly that the process would be uneconomical if the yield was less than about 90%.

More specifically this invention relates to a process for producing a high purity (at least 97% pure) tri-substituted triazine, in which the first step comprises substituting each of three chlorine (or other halogen) atoms on a tri-halo-s-triazine, specifically cyanuric chloride, with a polysubstituted piperazine, polysubstituted piperazin-2-one, polysubstituted 1,4-diazacycloheptane, polysubstituted 1,4-diazacycloheptan-2-one, or polysubstituted piperidine (each of which substituents are referred to by the acronym "PSP" for brevity). The desired tri-substituted triazine, referred to as PIP-T for brevity, therefore has a PSP substituent at each of the 2, 4 and 6 positions of the triazine ring.

In a conventional process for making the PIP-T, finely divided solid cyanuric chloride is reacted with the amine from which the PSP substituent is derived (this amine is referred to herein as "the PSP amine", or simply "the amine") in a large excess of solvent with little regard to how much is required to maintain a saturated solution of the components in solution. More solvent was used than is required to dissolve the solid cyanuric chloride and the PSP amine, with the expectation that the solvent will provide the medium in which the reaction may proceed with less restraint than if no solvent was used. The solvent provides a liquid phase in which the exothermic reaction proceeds controllably, and, in as little time as is safely practical. It will be appreciated that another cyanuric halide such as cyanuric bromide could also be used, but from a commercial point of view, only cyanuric chloride is practical.

These considerations dictated that such a solvent be chosen to provide the dual function of furnishing a relatively large heat sink from which, in turn, heat could be released to a cooling medium through the internal cooling coils of a reactor, or its jacket. Therefore, in the earliest process, the amine reactant was dissolved in a large excess of an alkylbenzene solvent; a strong base, such as an alkali metal hydroxide e.g. sodium hydroxide, and the cyanuric halide, usually cyanuric chloride, were then added gradually, both preferably as finely divided solids, to the solution. The base provided a catalytic function, and, as the reaction proceeded, chloride ions were generated (from the cyanuric chloride) forming HCl acid which was promptly neutralized by the NaOH. The reaction mass in the reactor was heated to conduct the reaction, then cooled after completion of the reaction, by a suitable heat exchange means (such as a cooling jacket on the reactor, or an internal cooling coil). The desired tri-substituted triazine was then recovered from the reaction mass by a conventional "work-up" in which the sodium chloride was washed away in hot water, and the solvent distilled from the toluene solution. This process is referred to as the "solvent process" disclosed in copending patent application Ser. No. 526,194 filed May 21, 1990 to Son et al.

Operation of this "solvent process" suffered from the serious disadvantage of corrosion of the reactor due to the presence of hot caustic and the generation of chloride ions under operating conditions which required a high temperature, well above the boiling point of the solvent at atmospheric pressure. The pressure generated in the reactor (which was related to the solvent used, and the amount of water present, if any), and the related high temperature (about 175° C.-200° C.) were required because of the difficulty of adding the third (and last) PSP substituent on the triazine ring. When an aqueous solution of concentrated NaOH (rather than solid NaOH) is used to facilitate its addition to the reactor, the contribution of the vapor pressure of the water exacerbates the problem of coping with pressure generated in the reactor.

Corrosion is a key contributor to "color" of the product. Therefore, not only is the profitability of operating a pressurized reactor at elevated temperature greatly diminished by the corrosion problem, but also the marketability of the PIP-T product. Unacceptably colored product which is not generally marketable has a "melt absorptivity" greater than 3.5 Ml/gm.cm determined as described hereinafter.

It will now be appreciated why it is difficult to add the third PSP substituent (referred to as the "last PSP substituent") under temperature and pressure conditions conducive to making substantially pure product, without incurring an unacceptable level of degradation of the product. Because the catalyst used in the prior art processes was caustic, practicality dictated the use of aqueous NaOH, but because the onus of marketability of the product was not then a consideration, the prior art failed to emphasize that degraded product is unmarketable if it is colored.

Even had it not been so desirable to add aqueous concentrated NaOH to the reactor in the solvent process, the problems of obtaining large quantities of anhydrous toluene, and maintaining operation of the system under truly anhydrous conditions was impractical.

From an appraisal of the foregoing facts it will now be evident that the problem to be solved has three distinct facets, namely (1) to make the desirably white tri-substituted triazine, (2) to control the corrosion of the reactor to a tolerable level, and (3) to recover and separate both the PIP-T product and the unreacted PSP amine without losing so much of either as to make the process uneconomical.

What is not evident from the foregoing clear enunciation of the problems to be solved, is that one must meet the requirements of marketability and economic production despite the impracticality of maintaining an anhydrous reaction system in a large reactor, say at least 100 gallons, such as is used for commercial preparation of the PIP-T stabilizer. The presence of a trace of moisture coupled with the unavoidable generation of chloride ions during the reaction, causes such severe corrosion even in a stainless steel reactor that not only is the product formed colored, but the reactor is damaged.

To cope with the problems of purity, yield and corrosion in the solventless process without using an Inconel or other uneconomical special alloy reactor, we devised a process, not long ago, in which neither a solvent (such as toluene) nor strong base (sodium hydroxide) catalyst was used. In this process, described in copending U.S. patent application Ser. No. 07/364,342 filed June 9, 1989, and incorporated by reference thereto as if fully set forth herein, a large excess of substantially anhydrous PSP amine is reacted with solid cyanuric chloride, the excess of amine used being in the range from 2 to 10 times the theoretical amount required to displace each of the Cl atoms of the cyanuric chloride, with the result that the last substituent was made in less than 12 hr.

That portion of the PSP over stoichiometric which was not used to provide the three PSP substituents, reacted with the HCl formed during the reaction, forming a PSP amine.Hcl salt (hereafter the "salt"). An alkanol (methanol) and concentrated aqueous solution of base (NaOH) was then added to neutralize the PSP amine.HCl, and form NaCl. The metered amount of methanol and water added, allowed at least 90% of the NaCl to be precipitated and filtered so as to leave the PIP-T solid which could be separated from the filtrate.

This filtrate had the peculiar property of being able to deliver white solid PIP-T particles when more water was added to the filtrate. The PIP-T particles could then be recovered, as could the excess amine reactant, methanol and water. This process is referred to as the "solventless process" because no solvent was used during the reaction in which each of the three PSP substitutions was made.

The foregoing solventless process, however, relied upon essentially complete separation of the PIP-T product from the PSP amine, and, recovery of the excess PSP amine for its economic viability, criteria which were not easily met under the conditions of that process. Moreover, because it was neither practical to obtain large quantities of reactant amine in an anhydrous state, nor to operate such an anhydrous reaction system on a commercial scale because traces of moisture were always present, the reactor was still prey (though to a lesser extent than in the solvent system) to corrosion.

In the relatively recent aforementioned "solvent" process we encountered the novel problem of unexpectedly severe corrosion even in a Hastelloy reactor. In the even more recent "solventless" process we tried, with some success, to solve the twin problems of separating the product PIP-T we made, and to recover the excess PSP amine we used. Since economics mandate the use of a stainless steel or glass-lined reactor (if a carbon steel one is impractical), along with effective recovery of essentially all the PIP-T made, not to mention the PSP amine, we were driven to explore still other routes to a fast and efficient process which substantially avoided the problems of both the "solvent" and the "solventless" processes.

It is this exploration which opened the door to the discovery that, in a limited amount of alkylbenzene solvent, preferably less by weight than the amount of amine used in the reaction, the PSP amine.HCl salt formed during the reaction, appears to speed up the reaction. Despite the relatively short period of reaction for the solventless process compared to that required for the solvent process, this "in situ catalytic effect" of the PSP amine.HCl salt went unrecognized in the solventless process, because of the large excess of amine present there. It was because of this in situ catalytic effect, no caustic catalyst was then, nor is now, required.

By "excess" of amine we refer to more than is required over theoretical to make the tri-substituted product. 3 mols of amine are theoretically required to make one mol of the product with one mol of cyanuric chloride. It takes an extra mol of amine (over theoretical to make the product) to react with the chloride ions generated. Thus it takes a minimum of 6 mols of amine to make 1 mol of product with our process. To ensure that all the chloride ions are reacted we use additional amine but less than 2 mols of amine for each chloride ion, so that we use less than 12 moles of amine for each mol of product made in the present process, referred to as the "hybrid" process.

Each of the several subsequent steps required for the work-up of the product, and recovery of the excess of amine deliberately used in our hybrid process (so termed for reasons which will now be more apparent), takes advantage of the peculiar physical characteristics of the solubility of each of the reactants and the reaction products. The ability to do this successfully, provides a solution to problems which adversely affected the economics of both the solvent and the solventless processes. Such steps, together provide a highly effective hybrid process for making the PIP-T product.

With particular regard to the effects of corrosion even in a stainless steel reactor, it will be recognized that, economics dictate that the presence of moisture which is responsible for such corrosion, can only be minimized, not excluded. Because of the relatively much smaller quantities of PSP amine (relative to the solventless process) and toluene (relative to the solvent process) required in the hybrid process, using a stainless steel reactor becomes economical. It will be also be recognized that, if a carbon steel reactor is used, the side reactions may be destructive and at the same time, generate much color. The color would have to be removed at a later stage, at great cost. Therefore, a carbon steel reactor is uneconomical, and either glass-lined or stainless steel reactors are chosen.

SUMMARY OF THE INVENTION

It has been discovered that the reaction of cyanuric chloride with an amine reactant ("PSP amine") can be completed in a relatively short time without a caustic catalyst in a pressurized reactor, and provide three substituents on the triazine ring, each substituent having a saturated heterocyclic amine group, if enough alkylbenzene solvent is used, sufficient only to maintain a near-saturated reaction mass of the PIP-T product, PSP amine.HCl salt and PSP amine at a temperature and pressure at which the reaction mass is to be washed upon completion of the reaction.

It has also been discovered that, despite the presence of traces of moisture, the instant "hybrid" process unexpectedly (a) avoids the corrosion problem typically associated with the generation of chloride ions (during the reaction) in the presence of hot caustic in the solvent process; (b) avoids the economically debilitating loss of PIP-T product and PSP amine reactant suffered incident to the separation of the former, and recovery of the latter used in necessarily very large excess in the solventless process; and, (3) avoids making a product PIP-T having a melt absorptivity greater than 3.5 mL/gm.cm. To obtain the foregoing results the process preferably requires from 6 to about 9 moles of PSP amine, more preferably, from 6 to 7 moles of amine for each mole of cyanuric chloride to be reacted.

It is therefore a general object of this invention to provide an improved "hybrid" process for the manufacture of a PIP-T, comprising, reacting a concentrated solution of cyanuric chloride, and, an amine reactant having a boiling point in excess of 200° C., at a pressure in the range from about 25 psig to 100 psig, preferably from 40-50 psig, in the presence of trace amounts of moisture, less than 500 ppm (parts per million) in no more solvent than is required to form a near-saturated solution of PIP-T product, PSP amine.HCl salt and PSP amine at a temperature and pressure at which the reaction mass is to be washed upon completion of the reaction. The reaction is carried out with at least 1 (one) additional equivalent of the amine reactant over that theoretically required for each displaceable chlorine, but less than 2 additional equivalents. Preferably less than 1.5 equivalents for each of the three Cl atoms, are used. The result is that a stainless steel reactor may be used without a serious corrosion problem; and further, the process allows substantially complete recovery of excess PSP amine used.

It is also a general object of this invention to provide a process for producing an acceptably white PIP-T product about 97% pure, in an yield in excess of 90%, in a reaction zone operating at a pressure lower than that used in the solvent process, but at about the same or higher temperature. After the reaction is complete, the PIP-T is recovered from the reaction mass without using an alkanol, allowing a recovery of about 90% of the PSP amine not consumed.

It is a specific object of this invention to provide the process described hereinabove for making the last PSP substituent on a triazine ring at relatively high temperature up to about 190° C. while yet producing at least 97% pure PIP-T in excess of 90% yield, and at the same time recycling substantially all the toluene and excess PSP amine reactant used.

It is still another general object of this invention to provide a recovery process for the PIP-T made in the absence of a conventional caustic catalyst and in the presence of a limited amount of toluene, comprising, carrying out the tri-substitution of cyanuric chloride with the aforementioned limited amount of PSP amine; adding enough hot toluene to the reaction mass to solubilize all the PIP-T, salt and excess PSP amine so as to form a hot near-saturated solution; washing the solution with hot water to take advantage of the high partition coefficient for the PSP amine.HCl salt in a mixture of toluene and water, compared to that of the PIP-T; then separating more than 90%, preferably more than 95% by weight of the PIP-T in solution in the organic phase, and recycling the solvent and PSP amine in a 50%-90% by wt solution (of amine in toluene) after the aqueous phase is neutralized and the amine extracted.

It is a specific object of this invention to carry out the above hybrid process under moderate pressure, less than 50 psig, in a reaction zone in which corrosion is minimized by limiting the amount of moisture (which may enter with the specifically limited amounts of alkylbenzene solvent and PSP amine), in an otherwise essentially anhydrous system.

It is another specific object of this invention to operate an affordable reaction vessel under pressure without sacrificing either the yield or the purity of the product obtained in prior art processes, then to utilize the unique solubility characteristics of the solvent and the PSP amine to make it possible to recycle the excess PSP amine and the solvent to the reaction zone, resulting in an economical process.

BRIEF DESCRIPTION OF THE DRAWING

The foregoing and other objects and advantages of our invention will appear more fully from the following detailed description, made in connection with the accompanying drawing in which.

DETAILED DESCRIPTION OF A PREFERRED EMBODIMENT

Figure 1:
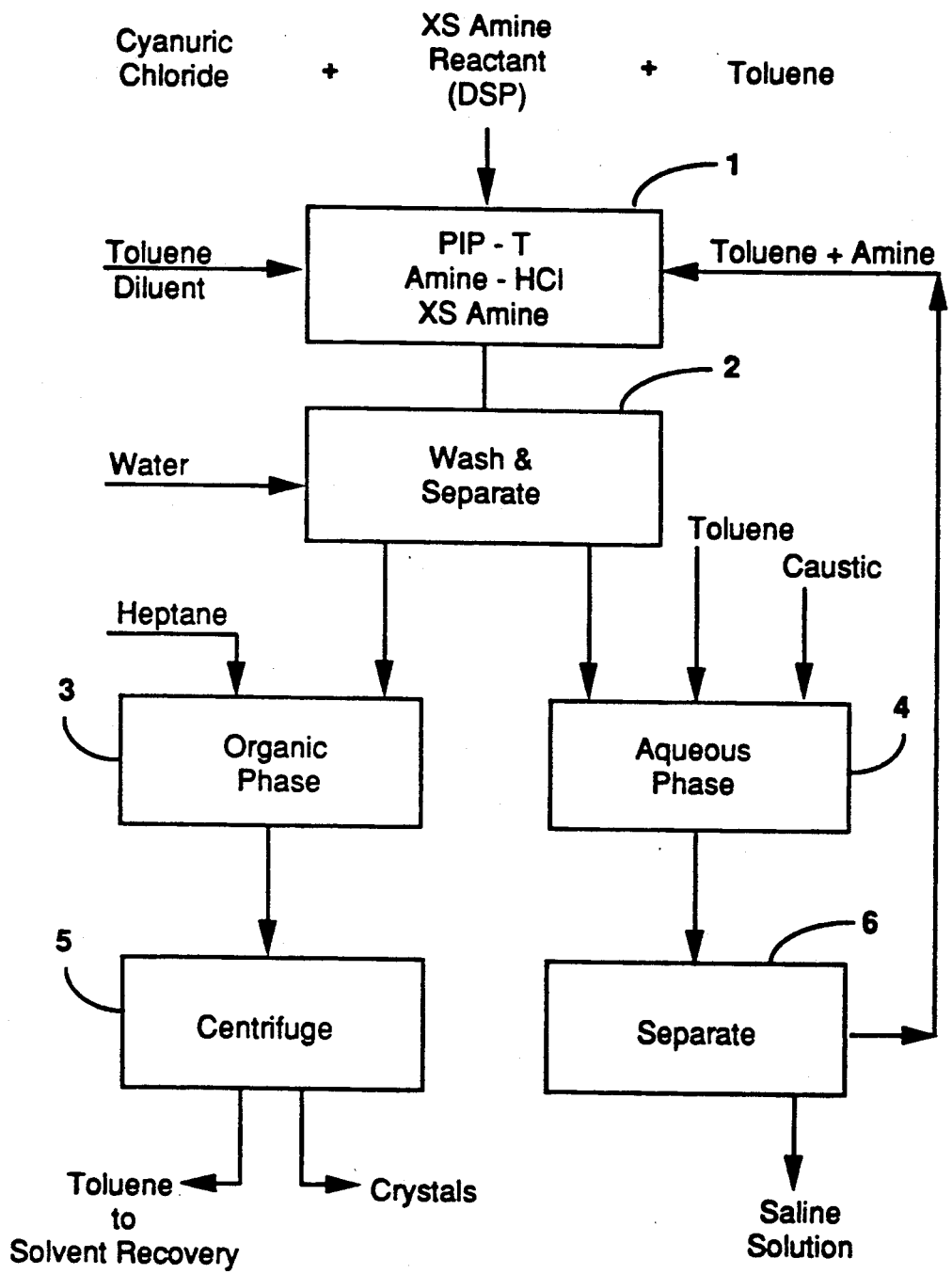
FIG. 1 is a flowsheet of the hybrid process, schematically illustrating the main steps.

In a preferred embodiment, the reaction is conducted with a limited amount of toluene, the ratio of toluene to PSP amine being in the range from about 1:2 to about 2:1 by weight. Preferably there is less solvent by weight than there is amine present, but more solvent than is required to form a saturated solution of cyanuric chloride in toluene at about 50° C.. Such limited amount, later, upon completion of the reaction, forms a near-saturated solution of both PIP-T product and PSP amine.HCl salt and unreacted PSP amine at the conditions under which the reaction product is to be washed with water. Though washing may be effected at elevated temperature in the range from about 90° C. to about 120° C., and correspondingly elevated pressure, it is preferred to wash at about 80° C. because this may be done at atmospheric pressure.

The PSP amine.HCl salt is generated by using excess amine in the aforementioned range, it being most preferred to use between 6.01 and 7 mols of amine for each mol of PIP-T product made. As the reaction proceeds, the PIP-T formed is dissolved in the toluene, and the HCl formed is immediately reacted with the excess amine reactant to form the salt which is also dissolved. The salt so formed catalyzes the reaction at low pressure so that the reaction proceeds to completion quickly, without either the yield or the purity of the product being deleteriously affected by the high temperature required (in the same range as required with the use of a large excess of toluene).

In addition to the economics of making the PIP-T product affordable, the amount of color contributed to a polymer which is stabilized by the PIP-T is of great importance to customers who are stabilizing light-colored polymers. The amount of color developed in the solid product is a function of the particular process steps used for making the compound. As stated hereinabove, the acceptability of product in the marketplace requires that it meet the criterion of color determined by a "melt absorptivity" no greater than 3.5 mL/gm.cm. Melt absorptivity is used as the criterion, because the polymer to be stabilized is typically extruded or otherwise thermoformed under elevated temperature sufficient to melt the stabilizer. The test is used to measure the color contribution of the stabilizer.

To measure the melt absorptivity one takes an accurately weighed small sample of the stabilizer (typically 0.2500 gm) in a 10 ml flask, and purges the sample with nitrogen. The flask is then placed in a Woods metal bath at 250° C. and removed after exactly 5 mins. The flask is allowed to cool and about 7 ml of isopropanol are added with repeated shaking and heating until the solid is all in solution. The solution is then cooled to 25° C. in a thermostated water bath at 25° C., and the solution diluted to 10 ml volume with more isopropanol.

The absorbance of the solution is then measured using a 420 nm light beam, this measurement being compared to that for pure isopropanol.

The net absorbance (As) is then calculated by subtracting the solvent background absorbance from that of the sample.

The absorptivity is then calculated as follows:

Absorptivity, $mL/gm.cm = As/bc = (As \times 10)/Ws$ where
b = sample cell path length in cm (1 cm)
c = sample solution concentration in g/mL and
Ws = weight of the sample used.

If placed against a white sheet of paper, the difference in color is visible to the naked eye. It is far more easily detected by an instrument such as a Lambda 9 Perkin Elmer UV-VIS NIR spectrophotometer.

The essential steps of the preferred process include, (1) reacting, in a solvent-controlled reaction zone, under essentially anhydrous conditions, a near-saturated solution of cyanuric chloride with a PSP amine reactant present in a molar excess, the amount of amine being in the range above 6 but less than 12 times the molar amount required to displace all the chlorine atoms in a mole of cyanuric chloride, in the absence of an alkaline catalyst, at a temperature in the range from about 150° C. to about 200° C., and a pressure in the range from about 25 psig to 100 psig, the amount of alkylbenzene solvent used being sufficient to maintain a near-saturated solution of the reaction mass of PIP-T product, PSP amine.HCl salt and PSP amine at 80° C. and atmospheric pressure;

(2) washing the reaction mass with water to remove substantially no PIP-T product but substantially all PSP amine.HCl salt and unreacted PSP amine in an aqueous solution;

(3) neutralizing the PSP amine.HCl salt with aqueous alkali to form an aqueous saline solution of PSP amine;

(4) extracting said aqueous saline solution of PSP amine with alkylbenzene solvent to obtain an organic extract containing the PSP amine, separate from the remaining aqueous raffinate;

(5) separating excess alkylbenzene solvent from the organic extract so as to obtain a concentrated solution of PSP amine containing at least the amount of solvent to be added in the reaction zone;

(6) recycling the concentrated solution containing the appropriate limited amount of solvent to the reaction zone; and, (7) recovering the PIP-T product from the organic phase.

If desired, after step (1), after all the cyanuric chloride is reacted, the hot reaction mass may be diluted with additional hot alkylbenzene solvent, the amount of such diluent being sufficient to maintain the PIP-T product, PSP amine.HCl salt, and unreacted PSP amine in solution at atmospheric pressure and room temperature.

Since the PIP-Ts made by the process of this invention are stabilizers for synthetic resinous materials, and sold in commerce mainly for such purpose, it is essential that, irrespective of which specific PIP-T is made, it be at least 97% pure. The PIP-T is represented by the structure

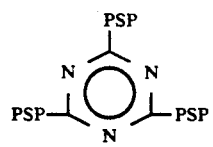

(I)

wherein PSP represents a substituent selected from the group consisting of structures (A)

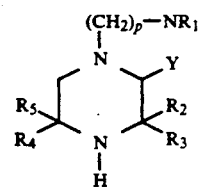

(II)

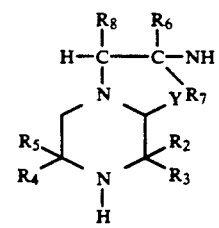

(III)

wherein,
Y represents H or —O,
$R_1$ represents $C_1$–$C_{24}$ alkyl, $C_5$–$C_{12}$ cycloalkyl, $C_7$–$C_{20}$ aralkyl or alkaryl, $C_1$–$C_{24}$ aminoalkyl, or $C_6$–$C_{20}$ aminocycloalkyl; $R_2$, $R_3$, $R_4$, and $R_5$ independently represent $C_1$–$C_{24}$ alkyl; and $R_2$ with $R_3$, or $R_4$ with $R_5$ are cyclizable to $C_5$–$C_{12}$ cycloalkyl including the $C^3$ and $C_5$ atoms respectively, of the piperazin-2-one ring;
$R_6$ and $R_7$ independently represent $C_1$–$C_{24}$ alkyl, and polymethylene having from 4 to 7 carbon atoms which are cyclizable;
$R_8$ represents H, $C_1$–$C_6$ alkyl, and phenyl; and,
p represents an integer in the range from 2 to about 10;

(B)

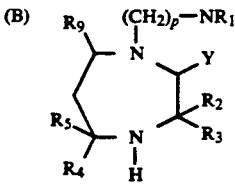

(IV)

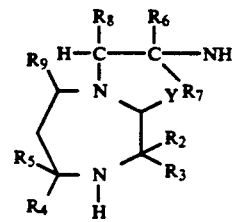

(V)

wherein, $R_9$ represents $C_1$–$C_{24}$ alkyl, the other substituents have the same connotation as given above; and, (C) 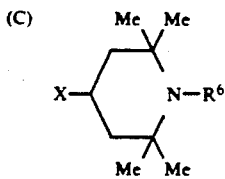 (VI)

wherein
Me=methyl

R$^6$ represents hydrogen, oxyl oxygen, C$_1$–C$_{12}$-alkyl, C$_3$–C$_7$-alkenyl, C$_7$–C$_{11}$-phenyl-alkyl, cyanomethyl, C$_2$–C$_{18}$-alkanoyl, or C$_3$–C$_{18}$-alkenoyl, or a group —CON(R$^7$)(R$^8$) in which R$^7$ is C$_1$–C$_{12}$-alkyl, allyl, cyclohexyl, benzyl, phenyl, or C$_7$–C$_{12}$-alkylphenyl, and R$^8$ is hydrogen, C$_1$–C$_{12}$-alkyl, allyl or benzyl or R$^7$ or R$^8$ together with the N atom to which they are attached, form a 5-membered ring or 6-membered heterocyclic ring; and, X is a divalent group of the formula —O—, —N-H—C$_2$–C$_{18}$-alkyl, —NH—(CH$_2$)2—O— and the like.

Such triazines substituted with a polysubstituted piperazinone are referred to in U.S. Pat. Nos. 4,480,092 to Lai and Son, and 4,629,752 to Layer, Son and Lai. Other PIP-Ts tri-substituted with polysubstituted piperidyl groups are referred to in U.S. Pat. No. 4,731,393 to Karrer.

The use of a limited amount of alkylbenzene solvent as a heat-dissipation agent, typically in the range from about 5:1 to about 10:1 by weight of solvent:cyanuric chloride, results in the formation of a solution of cyanuric chloride in the alkylbenzene solvent, or, more preferably a saturated solution. The addition of a liquid PSP amine improves the solubility of the cyanuric chloride as the displacement of chlorine atoms commences forming HCl which is complexed by excess PSP amine present. Though a xylene may be used as the solvent, toluene is preferred.

The preparation of a particular PIP-T formed by the reaction of cyanuric chloride with 4-(n-butylamino)-2,2,6,6-tetramethylpiperidine is represented by the structure

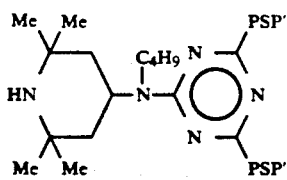 (VII)

wherein Me=methyl, and PSP, represents the same structure written for the other substituent on the triazine ring.

Other crystallizable PIP-Ts which are trisubstituted with polysubstituted piperidyl substituents are prepared with
4-(methylamino)-2,2,6,6,-tetramethylpiperidine;
4-(ethylamino)-2,2,6,6,-tetramethylpiperidine;
4-(n-propylamino)-2,2,6,6,-tetramethylpiperidine;
4-(isopropylamino)-2,2,6,6,-tetramethylpiperidine;
4-(isobutylamino)-2,2,6,6,-tetramethylpiperidine; etc.

Referring to FIG. 1 there is shown a flowsheet for the preparation of a particular PIP-T formed by the reaction of cyanuric chloride with a particular PSP amine reactant, 1-[2-(cyclohexylamino)ethyl]-3,3,5,5-tetramethylpiperazin-2-one, familiarly referred to as cyclohexylaminopiperazinone, and for brevity, as "CHP", represented by the structure

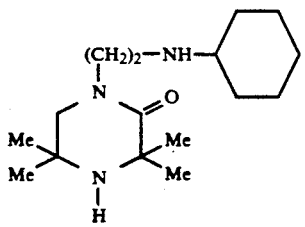 (VIII)

The structure of the desired PIP-T product is represented as follows:

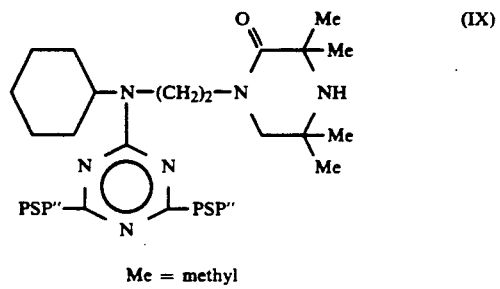 (IX)

Me = methyl wherein "PSP" represents the same structure given for the other substituent on the triazine ring.

Other crystallizable PIP-Ts which are trisubstituted with polysubstituted piperazin 2-one substituents are prepared with
1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]-3,3,5,5-tetramethylpiperazin-2-one;
1-[3-(cyclohexylamino)propyl]-3,3,5,5-tetramethylpiperazin-2- one; etc.

Still other crystallizable PIP-Ts which are trisubstituted with polysubstituted piperazine substituents are prepared with
1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine; and,
1-[3-(cyclohexylamino)propyl]-3,3,5,5-tetramethylpiperazine; inter alia.

In FIG. 1, the initial step of the process is shown as carrying out the reaction starting with PSP amine and cyanuric chloride reactants and solvent under pressure at a temperature in the range from about 175° C. to about 200° C., with toluene as solvent present in about an amount required to form a saturated solution of cyanuric chloride (in toluene) at about 20° C., and maintaining control of the exothermic reaction in a reaction zone indicated by reference numeral 1. It is preferred, for economic reasons, to use only sufficient toluene to maintain a near-saturated solution of PIP-T product, PSP amine.HCl salt and PSP amine at about 80° C. and atmospheric pressure. Using more toluene than is necessary vitiates reactor productivity.

The reaction zone is preferably a jacketed, cooled reactor fitted with an adequate mixing means, and a nitrogen line to flush the reactor with nitrogen. The reaction is complete when it is determined, by LC (liquid chromatographic) analysis (say) made periodically, that all the cyanuric chloride is tri-substituted. The HCl generated by displacement of the Cl reacts with the excess PSP amine reactant, forming the salt; and, all the PIP-T formed is dissolved in the hot toluene after the reaction is completed. In the flowsheet the reactor is shown to contain the PIP-T product formed, the salt (PSP amine.HCl), and the excess PSP.amine.

The reactor may be charged with a slurry of cyanuric chloride in toluene, the amount of toluene used being from about 75% to 95% of the total amount of toluene which will be required to keep the contents of the reactor in a near-saturated solution at about 80° C. The amine is then added to the reactor. An alternative is to add all the amine to the reactor, then add a near-saturated solution of cyanuric chloride in toluene containing in the range from about 25% to 30% by wt of cyanuric chloride at 20° C.

If necessary, hot toluene, in the range from about 50° C. -100° C. is added after reaction to the reaction mass as it is allowed to cool to and the reactor reaches atmospheric pressure, only enough being added so as to keep all the PIP-T product in solution at a temperature above 80° C.

The amount of toluene in the reaction zone now provides two functions, namely to lower the viscosity of the otherwise viscous mass, and to provide the appropriate partition coefficient when the diluted reaction mass is washed with water. Washing is typically done repetitively in a washing zone indicated by reference numeral 2, each time using about as much water by volume as there is toluene. After each wash with water at a temperature in the range from about 80° C. to about 100° C., the supernatant organic phase is decanted and collected in a recovery tank 3.

The organic phase in tank 3 is worked up conventionally to recover the PIP-T product as a white crystalline solid, and the toluene recycled. For example, enough heptane may be added to the organic phase to precipitate the PIP-T product which is recovered by centrifuging the mixture of crystals, heptane and toluene in centrifuge 5. The recovered crystals are dried and packaged. The toluene and heptane from the centrifuge 5 are led to a solvent recovery unit (not shown) and separated so that they may be reused.

The aqueous phase from the washing tank 2 is collected in a neutralization tank 4. The hot PSP amine.HCl in the aqueous phase from the washing zone, which aqueous phase contains some toluene, is neutralized with aqueous caustic, say 50% NaOH, in the tank 4. Upon neutralization, a saline solution is formed, regenerating the PSP amine. Sufficient alkali is added to maintain the pH above 10, preferably between 11 and 12. Hot toluene is added to this saline solution containing reconverted PSP amine (say, VIII) to extract the amine, using only enough toluene to form a concentrated solution of the amine. The mixture of toluene and aqueous phases is then separated in a decantation tank 6, and the concentrated solution of amine in toluene returned to the reactor 1.

The partition coefficient K of the PSP amine between toluene and water is defined as follows:

$$K = \frac{\text{(concentration of PSP amine in the toluene phase)}}{\text{(concentration of PSP amine in the aqueous phase)}}$$

is so favorable that typically more than 50%, often more than 80% by weight of the amine leaves the washing tank 2 with the first water wash. The organic phase may be given one or two final washes with acidified (about 37% HCl) hot water to convert any remaining PSP amine to the salt because the latter has a higher partition coefficient than the amine. This ensures that substantially all the PSP amine is washed and recovered from the product PIP-T solution in the toluene.

It is found that the efficiency of the hybrid process allows high productivity of the reactor ("reactor productivity"), at least 1 and typically more than about 2 lb PIP-T/gal of reactor volume without sacrificing purity and color of the product.

Figure 2:
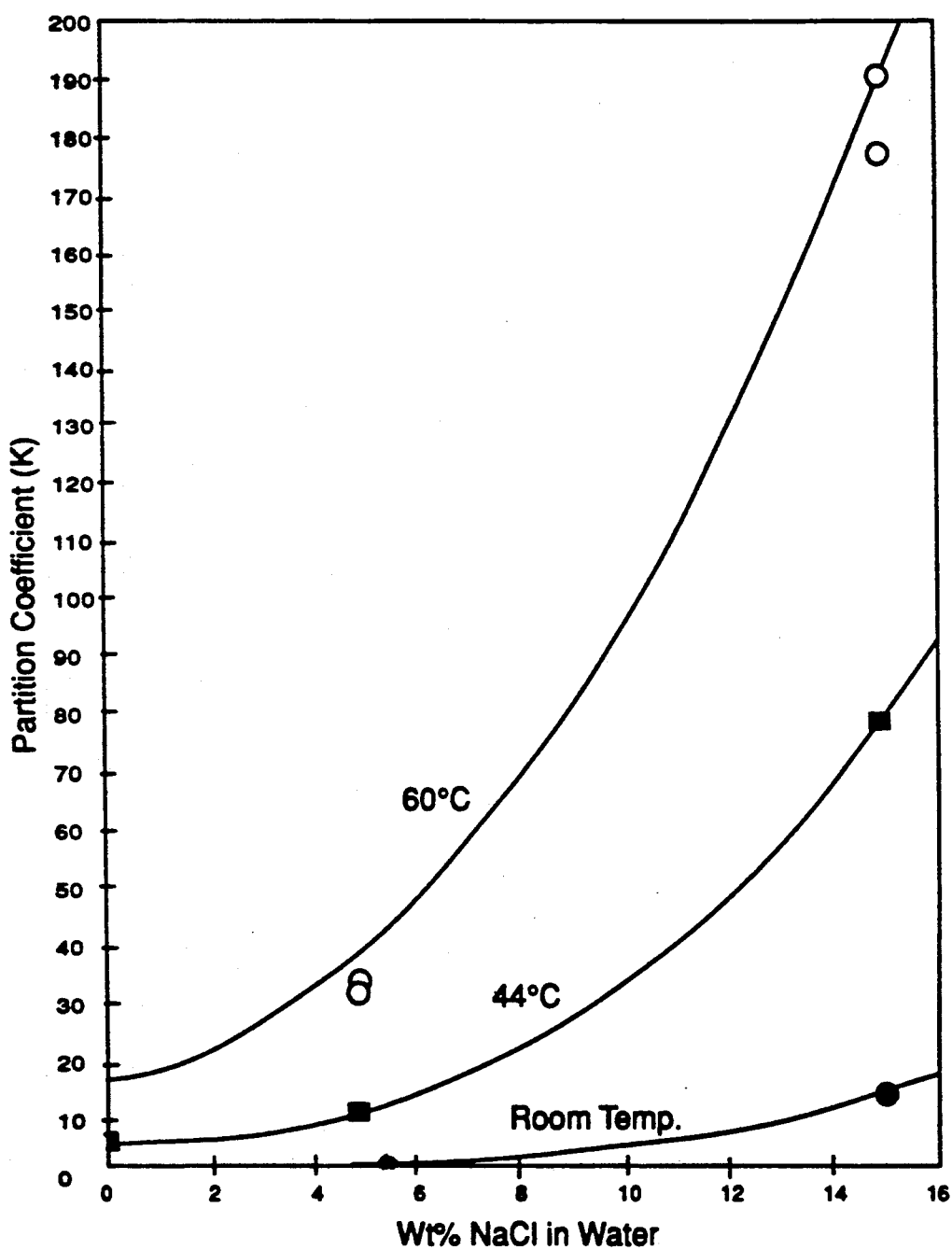
FIG. 2 is a graph showing the partition coefficient of a particular PSP amine, namely, 1-[2-(cyclohexylamino)ethyl]-3,3,5,5-tetramethylpiperazin-2-one, between toluene and a solution of salt (NaCl) in water, at three temperatures, namely room temperature (about 20° C.), 44° C. and 66° C.

Referring now to FIG. 2 there is shown a graph in which the partition coefficient of the compound (VIII) between toluene and water is plotted against the concentration of NaCl salt at different temperatures of the aqueous phase from the washing zone. It will be evident that the higher the concentration of salt in the aqueous solution, and the higher the temperature, the more (VIII) goes into the organic phase. Therefore, for optimum recovery of the (VIII), the extraction with toluene is done in as concentrated and hot an aqueous saline solution as is economical and consistent with the requirement for trouble-free operation of the unit. A preferred recycle stream has a concentration in the range from about 50% to about 95% by weight of PSP amine at the temperature in the recycle line. The actual amount of PSP amine in the recycle stream will depend upon the partition coefficient for the particular PSP amine used, and its solubility in toluene, each of which properties will vary depending upon the structure of the PSP amine.

Under such circumstances it is possible to use only as much toluene as is required in the reaction zone to carry out the reaction. The solution of (VIII) in toluene is then recycled to the reaction zone as shown. If more toluene is used than is required during the reaction, which may deliberately be done, the excess toluene is stripped from the solution. The recycle stream is flowed to a stripping column (not shown) where the excess toluene is stripped overhead. This ensures that if any water is present, it is stripped away, along with the toluene removed.

The conventional work up of the organic phase as described above is facilitated because the organic phase typically contains at least 30% by weight PIP-T. An alternative process to recover the PIP-T crystals is simply to distill off the toluene.

Since there is essentially no PIP-T or PSP amine left in the saline solution after extraction with toluene, the saline solution is discarded.

The following illustrative example provides data for the foregoing hybrid process to prepare the compound (VIII) on a large scale.

EXAMPLE 1

Preparation of the PIP-T represented by the structure IX

About 440 lb, about half of which is from a recycle stream, of substantially anhydrous 1-[2- cyclohexylamino)-ethyl]-3,3,5,5-tetramethylpiperazin-2-one (VIII) having a mol wt of 281.45, 47.5 lb of cyanuric chloride and 313 lb of toluene are charged to a dry jacketed and cooled stainless steel reactor and the reaction commenced at about 60° C. The temperature is allowed to rise to about 175° C. and the reaction is completed at this higher temperature.

The PIP-T, the PSP amine.salt and excess PSP amine are maintained in a near-saturated solution in hot toluene. The PIP-T is far more soluble in hot toluene, and much less soluble in water, than is the salt or PSP amine, so that the salt and excess PSP amine are washed out of the hot toluene solution with hot water.

Instead of dumping the contents of the reactor to a washing zone, they are washed in the reactor. Additional hot toluene at about 90° C. may be added to the reaction mass to facilitate washing and the reactor and its contents allowed to cool to about 100° C. when the reaction mass is washed with hot water until substantially all the salt formed, and the unreacted amine are washed out of the organic phase.

The organic phase is then mixed with 65 gals of heptane and about 230 lb of PIP-T product precipitated and recovered. About 310 lb of toluene with about 10 lb of unreacted amine are recovered for reuse. Unwanted byproducts are about 7 lb.

The aqueous phase, about 1600 lb, is neutralized with 62 lb of 50% by wt NaOH, and extracted with 313 lb of toluene which dissolve about 200 lb of (VIII). The solution of (VIII) in toluene is recycled to the reactor. The 1645 lb of depleted aqueous phase (31 lb water come in with the caustic solution, and 14 lb of water are made during the neutralization) contains the 31 lb alkali, a trace of toluene and about 12 lb (VIII). In the preferred operation, product having a melt absorptivity in the range from about 1 to 3 mL/gm.cm is made in better than 90%, often better than 95% yield while maintaining a reactor productivity in the range from about 1-3 lb/gal. The combination of the foregoing makes the difference between providing an affordable stabilizer, and one which cannot be sold.

It will now be evident that the use of a near-saturated solution in the reactor is to minimize the amount of solvent to be handled in system, yet, without running the risk of premature precipitation of solid. Typically "near-saturation" refers to a solids content within about 5% of saturation.

Having thus clearly and objectively stated the problems to be solved in the "solvent" and "solventless" processes, and also having shown how to solve the problems by the invention disclosed herein, and having provided a detailed description and illustrations of the best mode of practicing this invention, it is to be understood that no undue restrictions are to be imposed by reason thereof, and particularly that the invention is not restricted to a slavish adherence to the details set forth herein.

We claim:

1. A process for preparing a 2,4,6-substituted-1,3,5-triazine having a substituted heterocyclic amine substituent at each 2-,4-, and 6- positions, referred to as a tri-substituted triazine or PIP-T, said substituent being derived by a substitution reaction from a compound selected from the group consisting of a polysubstituted piperidine, polysubstituted piperazine, polysubstituted piperazine-2-one, polysubstituted 1,4-diazacycloheptane, and polysubstituted 1,4-diazacycloheptan-2-one, each referred to as a PSP amine reactant, said process comprising, (1) reacting in a solvent-controlled reaction zone, under essentially anhydrous conditions, a concentrated solution of cyanuric chloride with said PSP amine reactant present in an excess over stoichiometric in the range above 1 but less than 2 equivalents of amine required to displace each chlorine atom of the cyanuric chloride, in the absence of an alkali catalyst, at a temperature in the range from about 150° C. to about 200° C., and a pressure in the range from about 25 psig to 100 psig, the amount of alkylbenzene solvent used being sufficient to maintain a near-saturated solution of a reaction mass of PIP-T product, PSP amine.Hcl salt and PSP amine under conditions for washing after completion of the reaction;

(3) washing said near-saturated reaction mass with water to remove substantially no PIP-T product but substantially all PSP amine.HCl salt and unreacted PSP amine in an aqueous solution;

(4) neutralizing the PSP amine.HCl salt with aqueous alkali to form an aqueous saline solution of PSP amine;

(5) extracting said aqueous saline solution of PSP amine with a limited amount of alkylbenzene solvent to obtain an organic extract containing the PSP amine, said limited amount being enough to dissolve at least 90% of the unreacted PSP amine; and, (6) recovering the PIP-T product from the organic phase.

2. The process of claim 1 including after step (5), recycling the concentrated solution containing the appropriate limited amount of solvent to the reaction zone.

3. The process of claim 1 wherein said tri-substituted triazine (PIP-T) is represented by the structure

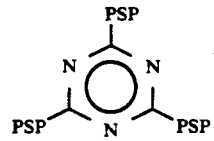

wherein PSP represents a substituent selected from the group consisting of structures

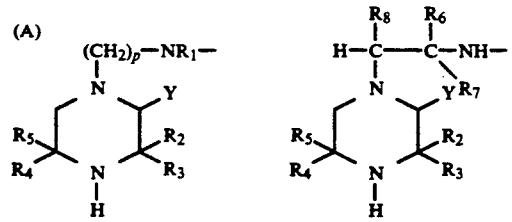

wherein,

Y represents H or =O, $R_1$ represents $C_1$-$C_{24}$ alkyl, $C_5$-$C_{12}$ cycloalkyl, $C_7$-$C_{20}$ aralkyl or alkaryl, $C_1$-$C_{24}$ aminoalkyl, or $C_6$-$C_{20}$ aminocycloalkyl; $R_2$, $R_3$, $R_4$, and $R_5$ independently represent $C_1$-$C_{24}$ alkyl; and $R_2$ with $R_3$, or $R_4$ with $R_5$ are cyclizable to $C_5$-$C_{12}$ cycloalkyl including the $C^3$ and $C^5$ atoms respectively, of the piperazin-2-one ring;

$R_6$ and $R_7$ independently represent $C_1$-$C_{24}$ alkyl, and polymethylene having from 4 to 7 carbon atoms which are cyclizable; $R_8$ represents H, $C_1$-$C_6$ alkyl, and phenyl; and, p represents an integer in the range from 2 to about 10;

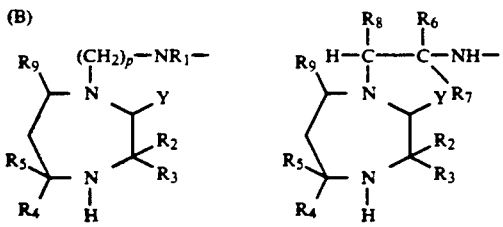

(B)

wherein, $R_9$ represents $C_1$-$C_{24}$ alkyl, and the other substituents have the same connotation as given above; and,

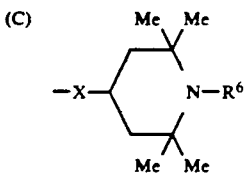

(C)                                                    (VI)

wherein
Me = methyl
$R^6$ represents hydrogen, oxyl oxygen, $C_1$-$C_{12}$-alkyl, $C_3$-$C_7$-alkenyl, $C_7$-$C_{11}$-phenyl-alkyl, cyanomethyl, $C_2$-$C_{18}$-alkanoyl, or $C_3$-$C_{18}$-alkenoyl, or a group —CON($R^7$)($R^8$) in which $R^7$ is $C_1$-$C_{12}$-alkyl, allyl, cyclohexyl, benzyl, phenyl, or $C_7$-$C_{12}$-alkylphenyl, and $R^8$ is hydrogen, $C_1$-$C_{12}$-alkyl, allyl or benzyl or $R^7$ or $R^8$ together with the N atom to which they are attached, form a 5-membered ring or 6-membered heterocyclic ring; and,
X is a divalent group of the formula —O—, —N-H—$C_1$-$C_{18}$-alkyl, and, —NH—(CH$_2$)$_2$—O—.

4. The process of claim 3 wherein, after all the cyanuric chloride is reacted in step (1), diluting the hot reaction mass with additional hot alkylbenzene solvent, the amount of such diluent being sufficient to maintain the PIP-T product, PSP amine.HCl salt, and unreacted PSP amine in solution at atmospheric pressure and room temperature.

5. The process of claim 3 including, after step (5) and before step (6), separating excess alkylbenzene solvent from the organic extract so as to obtain a concentrated solution of said PSP amine in alkylbenzene solvent in an amount at least sufficient to provide said near-saturated solution.

6. The process of claim 3 wherein said alkylbenzene solvent in step (1) is toluene present in a ratio of toluene: PSP amine in the range from about 1:2 to about 2:1 by weight.

7. The process of claim 3 wherein said alkylbenzene solvent in step (1) is toluene present in a ratio of toluene: cyanuric chloride in the range from about 5:1 to about 10:1 by weight.

8. The process of claim 6 wherein said alkylbenzene solvent is toluene used only in an amount sufficient to maintain a near-saturated solution of PIP-T product, PSP amine.HCl salt and PSP amine at about 80° C. and atmospheric pressure; and, said washing in step (3) is carried out at 80° C. and atmospheric pressure.

9. The process of claim 7 wherein in step (5) only enough of said toluene is used to provide about a 50% to 95% concentrated solution of amine in toluene at the temperature in the recycle line to the reactor.

10. The process of claim 9 wherein said PSP amine has said structure (A).

11. The process of claim 9 wherein said PSP amine has said structure selected from the group consisting of (B) and (C).

12. The process of claim 9 wherein said PSP amine having a structure selected from the group consisting of (A) (B) and (C) has a melt absorptivity no greater than 3.5 mL/gm.cm.

13. The process of claim 12 wherein said PSP amine is selected from the group consisting of
1-[3-(isopropylamino)propyl]-3,3,5,5-tetramethylpiperazin-2-one;
1-[2-(isopropylamino)ethyl]-3,3,5,5-tetramethylpiperazin-2-one;
1-[2-(butylamino)ethyl]-3,3,5,5-tetramethylpiperazin-2-one;
1-[3-(cyclohexylamino)propyl]-3,3,5,5-tetramethylpiperazin-2-one;
1-[3-(isopropylamino)propyl]-3,3,5,5-tetramethylpiperazine;
1-[2-(isopropylamino)ethyl]-3,3,5,5-tetramethylpiperazine;
1-[2-(butylamino)ethyl]-3,3,5,5-tetramethylpiperazine;
1-[3-(cyclohexylamino)propyl]-3,3,5,5-tetramethylpiperazine;
4-(methylamino)-2,2,6,6,-tetramethylpiperidine;
4-(ethylamino)-2,2,6,6,-tetramethylpiperidine;
4-(n-propylamino)-2,2,6,6,-tetramethylpiperidine;
4-(isopropylamino)-2,2,6,6,-tetramethylpiperidine; and,
4-(isobutylamino)-2,2,6,6,-tetramethylpiperidine.

14. In a process for preparing a 2,4,6-substituted-1,3,5-triazine having a substituted heterocyclic amine substituent at each 2-,4-, and 6- positions, referred to as a tri-substituted triazine or a PIP-T said substituent being derived by a substitution reaction from a compound selected from the group consisting of a polysubstituted piperidine, polysubstituted piperazine, polysubstituted piperazin-2-one, polysubstituted 1,4-diazacycloheptane, or polysubstituted 1,4-diazacycloheptan-2-one, each referred to as a PSP amine reactant, by reacting an excess of said PSP amine in the presence of an alkylbenzene solvent and in the absence of an alkali catalyst, under elevated temperature and pressure conditions in a temperature controlled reaction zone, and recovering said PIP-T product, the improvement comprising, contacting a solution of cyanuric chloride in said alkylbenzene solvent with said PSP amine reactant present in an excess over stoichiometric in the range above 1 but less than 2 equivalents of amine for each chlorine atom, at a temperature in the range from about 150° C. to about 200° C., and a pressure in the range from about 25 psig to 100 psig, the amount of said solvent being sufficient to maintain a saturated solution of PIP-T product, PSP amine.HCl salt and PSP amine at 80° C. and atmospheric pressure, whereby said PSP amine.HCl salt provides a catalytic function sufficient to provide at least a 90% yield of said PIP-T product having a purity of at least 95%, and essentially to negate the formation of byproducts having a deleterious effect on the color of said PIP-T product due to corrosion in said reaction zone, said color of said product being no greater than that which corresponds to a melt absorptivity of 3.5 mL/gm.cm.

15. The process of claim 14 wherein said alkylbenzene solvent is toluene present in a ratio of toluene: cyanuric chloride in the range from about 5:1 to about 10:1 by weight.

16. The process of claim 15 including washing said saturated solution with water to remove substantially no PIP-T product but substantially all PSP amine.HCl salt and unreacted PSP amine in an aqueous solution.

17. The process of claim 16 including adding sufficient aqueous alkali to neutralize said PSP amine.HCl and form its salt in an aqueous alkali metal chloride solution.

18. The process of claim 17 including extracting said PSP amine from an aqueous sodium chloride solution with a limited amount of toluene to obtain an organic extract containing the PSP amine, said limited amount being enough to dissolve at least 90% of the unreacted PSP amine and form a 50% to 95% concentrated solution of said amine in toluene at the temperature of extraction.

19. The process of claim 18 including recycling said concentrated solution of toluene to said reaction zone.

20. The process of claim 19 wherein said tri-substituted triazine (PIP-T) is represented by the structure

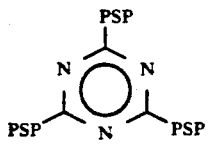

wherein PSP represents a substituent selected from the group consisting of structures (A)

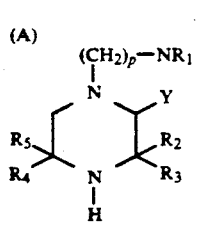

wherein,

Y represents H or =O, $R_1$ represents $C_1$–$C_{24}$ alkyl, $C_5$–$C_{12}$ cycloalkyl, $C_7$–$C_{20}$ aralkyl or alkaryl, $C_1$–$C_{24}$ aminoalkyl, or $C_6$–$C_{20}$ aminocycloalkyl;

$R_2$, $R_3$, $R_4$, and $R_5$ independently represent $C_1$–$C_{24}$ alkyl; and $R_2$ with $R_3$, or $R_4$ with $R_5$ are cyclizable to $C_5$–$C_{12}$ cycloalkyl including the $C^3$ and $C^5$ atoms respectively, of the piperazin-2-one ring;

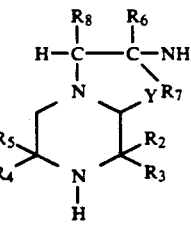

$R_6$ and $R_7$ independently represent $C_1$–$C_{24}$ alkyl, and polymethylene having from 4 to 7 carbon atoms which are cyclizable;

$R_8$ represents H, $C_1$–$C_6$ alkyl, and phenyl; and, p represents an integer in the range from 2 to about 10;

(B)

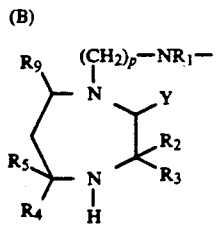 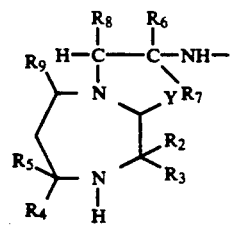

wherein, $R_9$ represents $C_1$–$C_{24}$ alkyl, and the other substituents have the same connotation as given above; and, (C)                    (VI)

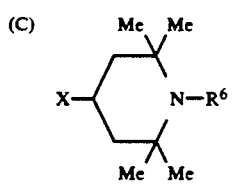

wherein

Me = methyl $R^6$ represents hydrogen, oxyl oxygen, $C_1$–$C_{12}$-alkyl, $C_3$–$C_7$-alkenyl, $C_7$–$C_{11}$-phenyl-alkyl, cyanomethyl, $C_2$–$C_{18}$-alkanoyl, or $C_3$–$C_{18}$-alkenoyl, or a group —CON($R^7$)($R^8$) in which $R^7$ is $C_1$–$C_{12}$-alkyl, allyl, cyclohexyl, benzyl, phenyl, or $C_7$–$C_{12}$-alkylphenyl, and $R^8$ is hydrogen, $C_1$–$C_{12}$-alkyl, allyl or benzyl or $R^7$ or $R^8$ together with the N atom to which they are attached, form a 5-membered ring or 6-membered heterocyclic ring; and, X is a divalent group of the formula —O—, —NH—$C_1$–$C_{18}$-alkyl, and, —NH—$(CH_2)_2$—O—.

21. The process of claim 20 wherein said alkylbenzene solvent is toluene present in a ratio of toluene: PSP amine in the range from about 1:2 to about 2:1 by weight.

22. The process of claim 21 wherein said PSP amine has said structure (A).

23. The process of claim 21 wherein said PSP amine has said a structure selected from the group consisting of (B) and (C).

24. The process of claim 22 wherein the efficiency of the process is characterized by a reactor productivity of about 2 lb PIP-T product per gallon of volume in said reaction zone.

* * * * *